United States Patent [19]
Grantham

[11] Patent Number: 5,069,660
[45] Date of Patent: Dec. 3, 1991

[54] URETHRA PROSTHETIC FOR RELIEVING PROSTATIC PROBLEMS

[76] Inventor: David S. Grantham, Lot 39, Hardingsdale, Pietermaritzburg, South Africa

[21] Appl. No.: 447,269

[22] Filed: Dec. 7, 1989

[30] Foreign Application Priority Data

Dec. 9, 1988 [ZA] South Africa .................. 88/9247

[51] Int. Cl.$^5$ ............................................. A61F 2/02
[52] U.S. Cl. ........................................ 600/30; 128/79; 623/10; 623/11
[58] Field of Search ............ 623/10, 11; 128/79; 600/30

[56] References Cited

U.S. PATENT DOCUMENTS

| | | | |
|---|---|---|---|
| 4,204,530 | 5/1980 | Finney | 128/79 A |
| 4,387,705 | 6/1983 | Finney | 600/30 |
| 4,523,584 | 6/1985 | Yachia et al. | 128/79 A |
| 4,559,055 | 12/1985 | Ogunro | 623/11 |
| 4,769,038 | 9/1988 | Bendavid et al. | 623/11 |
| 4,819,623 | 4/1989 | Ogunro | 623/11 |
| 4,878,890 | 11/1989 | Bilweis | 623/11 |

FOREIGN PATENT DOCUMENTS

| | | |
|---|---|---|
| 0221570 | 5/1987 | European Pat. Off. . |
| 0274846 | 7/1988 | European Pat. Off. . |
| 0323818 | 7/1989 | European Pat. Off. . |
| 1183497 | 3/1970 | United Kingdom . |
| 1316240 | 5/1973 | United Kingdom . |
| 2011260 | 7/1979 | United Kingdom . |
| 2077107 | 12/1981 | United Kingdom . |
| 2090143 | 7/1982 | United Kingdom . |

*Primary Examiner*—Richard J. Apley
*Assistant Examiner*—Lynne A. Reichard
*Attorney, Agent, or Firm*—Kenyon & Kenyon

[57] ABSTRACT

The invention relates to a prosthetic device for keeping open the lumen of a prostatic urethra. The device includes a body of a physiologically acceptable, perforated, resilient material that can be deformed into a channel-shaped configuration in which it can be inserted into a prostatic urethra. The resilience of the body, together with anchoring formations defined by the body ensures that the device is held secure and can be left indwelling in the prostatic urethra for keeping it open.

14 Claims, 2 Drawing Sheets

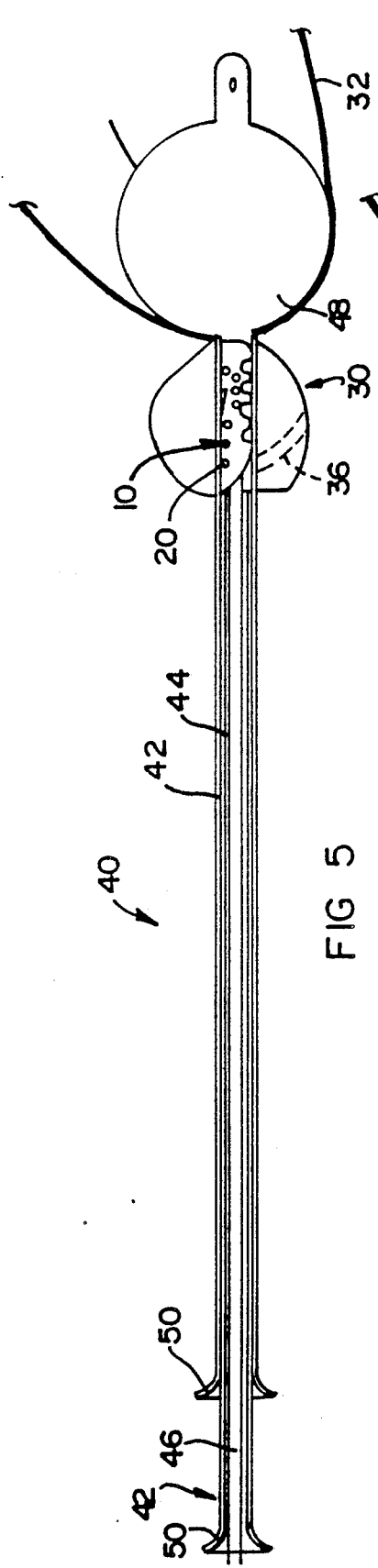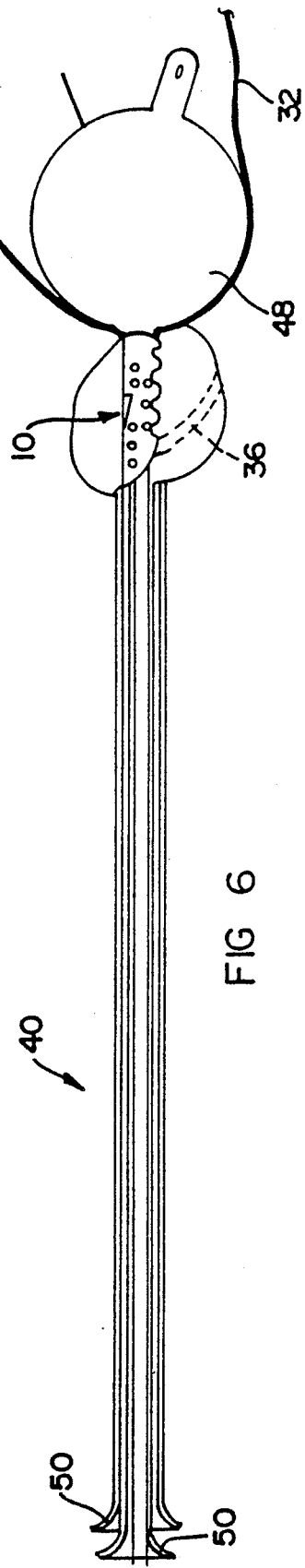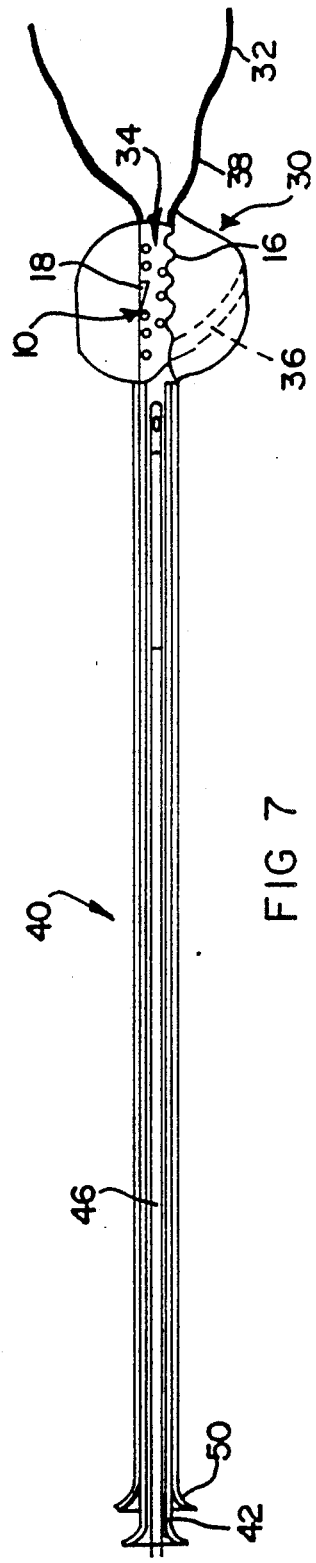

URETHRA PROSTHETIC FOR RELIEVING PROSTATIC PROBLEMS

THIS INVENTION relates to a prosthetic device.

Hypertrophy of the prostate, and other anomalies associated therewith, is part of the normal ageing process. Enlargement of the prostrate, is likely to put pressure on the prostatic urethra. This may cause stenosis and obstruct micturition. The bladder becomes painfully distended. The resulting urine retention may be relieved by dilatation by the passage of a bougie or a catheter up the urethra. However, this procedure can provide only symptomatic and temporary relief. Repeated catheterisation is required which may often cause traumatisation of the urethra. Eventually a prostatectomy procedure may be required.

According to this invention, a prosthetic device comprises a physiologically acceptable, perforated, resilient body which is channel-shaped in use, the inherent resilience of the body, in its channel-shaped configuration, permitting the lumen of a prostatic urethra being kept open, when the body is left indwelling in the prostatic urethra.

Suitable materials for the device are elastomeric polymers, such as TEFLON or silicon elastomers. Also, the body of the device may be lacquered with a coating of a vulcanized silicon elastomer.

The body of the device may be a planar tongue-shaped, resilient element which can be deformed to form its in use channel-shaped configuration. Typically, in use, the channel-shaped body has a horse shoe shaped end profile, the conical portion of the tongue shaped planar element providing a tapered end for the body in its in use channel-shaped configuration.

The channel-shaped body may be provided with anchoring formations. Typically, the edges of the channel-shaped body may be serrated and the surface of the channel-shaped body intended to be in contact with the inner wall of the prostatic urethra may be provided with wedge-shaped projections.

The invention will be understood, more clearly, from the following descriptions taken in conjunction with the accompanying drawings.

In the drawings,

FIGS. 5 to 7, illustrate in side view the method of implanting the prosthetic device of FIG. 1 in the prostatic urethra.

Figure 1:
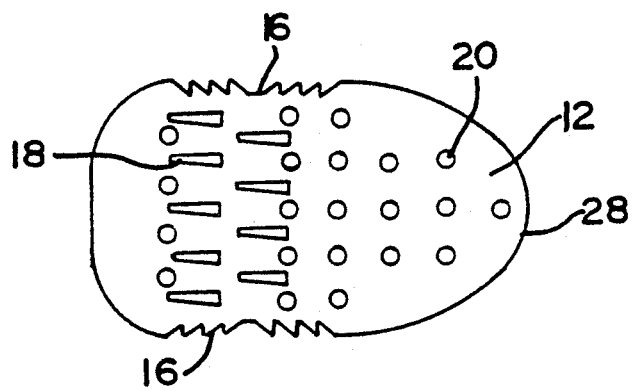
FIG. 1 is a plan view of a prosthetic device, in accordance with the invention, in an inoperative configuration.
Figure 2:
FIG. 2 is a side elevation view of the device as shown in FIG. 1.
Figure 3:
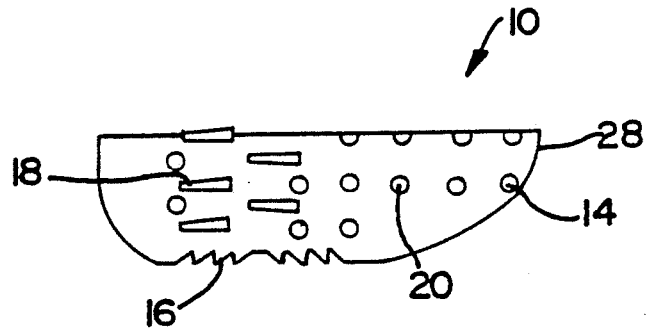
FIG. 3 is side elevation view of the prosthetic device of FIG. 1, in an in use, channel-shaped configuration.

Referring to FIG. 3 of the drawings, there is shown a prosthetic device generally indicated by the reference numeral 10. The prosthetic device 10, in use, comprises a resilient, perforated, channel-shaped body 14 formed by deforming a planar tongue-shaped element as shown in FIG. 1.

Figure 4:
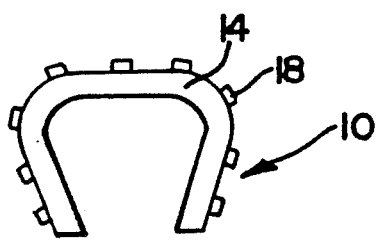
FIG. 4 is an end elevation view of the device as shown in FIG. 3.

The body 14 has anchoring formations in the form of serrations 16 along its sides and wedge-shaped projections 18 on the surface of the body which forms the outer surface of the channel-shaped body 14. Also, the body 14 is perforated with perforations 20. The serrations 16 and the wedge shaped projections 18 serve as gripping formations for anchoring the prosthetic device 10 in the prostatic urethra. The channel-shaped body 14 has a horse shoe type end profile in use, as particularly seen in FIG. 4, with a tapering end 28, as particularly seen in FIG. 3.

The length and other dimensions of the prostatic urethra can be endoscopically determined and these dimensions will determine the dimensions of the prosthetic device 10 and the dimensions of the tongue-shaped planar element forming the body 14.

Preferably, the length of the prosthetic device is such that in its indwelling configuration, it spans the prostatic urethra from the opening (neck) of the bladder right through the prostate, the inherent resilience of its resilient channel-shaped body 14 permitting straddling of the prostatic urethra for maintaining an open lumen.

In the male human body, the vas deferense and the seminal vesicle unite to form the ejaculatory duct which traverses the prostate to empty fluids into the prostatic urethra in the verumontanum region. A horse shoe profile has been selected for the channel-shaped body 14 so that an indwelling prosthetic device 10 implanted in the prostatic urethra, does not obstruct the flow of fluid from the ejaculatory duct.

The prostate produces prostatic secretions, which reach the prostatic urethra through a number of little ducts which empty into the prostatic urethra. Therefore, perforations 20 have been provided in a distal zone of the channel-shaped body 14 so that in its indwelling configuration in the prostatic urethra, the prosthetic device 10 does not block the flow of secretions from these little ducts.

Referring now to FIGS. 5 to 7, there is illustrated a method of implanting the prosthetic device 10 in the prostatic urethra.

The prostate generally is indicated by the reference numeral 30. The urinary bladder 32 is partially shown. The prostatic urethra 34 traverses the prostrate 30. The prostatic urethra 34 receives the ejaculatory duct 36 as well as the little prostatic ducts (not shown).

An instrument generally indicated by the reference numeral 40 is specially designed for the purpose of introducing the prosthetic device 10 in the prostatic urethra 34.

The instrument 40 comprises a set of three catheters 42, 44 and 46. The catheter 46 is a Foley's catheter. The catheters 42 and 44 are of physiologically acceptable material such as stainless steel or a polymer.

The diameter of catheter 44 is smaller than that of catheter 42. Thereby catheter 44 can be slidably displaced in the catheter 42. The inner diameter of the catheter 42 permits insertion of the prosthetic device 10 at one end of the catheter 44 as seen in FIG. 5. As particularly seen in FIG. 5, the tapering end 28 of the prosthetic device 10 is made to face inwards in the catheter 42. The catheter 44 is then inserted into the catheter 42 so that the end of catheter 44 abuts the prosthetic device 10. The Foley's catheter 46 having an inflatable bulb 48 is then inserted through the catheter 44. The inherent resilience of the prosthetic device 10 holds it in place in the catheter 42.

The instrument 40 is lubricated and inserted through the penile end of the urethra until its prosthetic device-bearing end extends into the bladder. The Foley's catheter 46 is then pushed forward gently until the bulb 48 of the Foley's catheter 46 can be inflated in the bladder 32 in the normal way. The Foley's catheter is then retracted against the neck 38 of the bladder 32. The inflated bulb 48 now serves as a datum point for implanting the prosthetic device 10 in the prostatic urethra. The outer catheter 42 is extended until the prosthetic device 10 abuts the inflated bulb 48. FIG. 5 illustrates this position. Then, the inner catheter 44 is held firm and the outer catheter 42 is retracted until the prosthetic device 10 is implanted in the prostatic urethra through its resilience. FIG. 6 illustrates this position. Now, the bulb 48 of the Foley's catheter 46 is deflated and the Foley's catheter 46 is retracted from the bladder. FIG. 7 illustrates this position of the instrument 40. The instrument 40 can now be retracted out of the urethra, after a cysto-urethroscopic examination of the implanted prosthetic device 10. Typically, the catheters 42 and 44 have flared proximal ends 50 for facilitating insertion, retraction and withdrawal. The catheters 42 and 44 are graduated near their flared ends 50 for precisely implanting the prosthetic device 10 in the prostatic urethra.

As seen in FIG. 7, the "open face" of the channel-shaped body 14 of the prosthetic device 10 faces the ejaculatory duct 36 in the region of the verumontanum. Therefore the prosthetic device 10 does not obstruct the normal flow of seminal fluid from the ejaculatory duct 36.

The serrations 16 allow the channel-shaped body 14 of the prosthetic device 10 to grip the inner wall of the prostatic urethra. The wedge shaped projections 18 basically serve the same purpose. Together, the serrations 16 and the wedge-shaped projections 18 prevent spasmodic migration of an indwelling prosthetic device 10.

Suitable materials for the prosthetic device 10 are physiologically acceptable elastomeric polymers, such as TEFLON or silicon elastomers. Also, the channel-shaped body 14 of the prosthetic device can be lacquered with a coating of a vulcanized silicon elastomer.

What is claimed is:

1. A urethra prosthetic device for insertion in a urethra comprising a planar tongue-shaped body said body being made of resilient material to permit resilient deformation of two sides thereof to impart a channel-shaped profile to said body for maintaining an open lumen in a urethra.

2. A prosthetic device as claimed in claim 1, in which the body is of an elastomeric polymer.

3. A prosthetic device as claimed in claim 1, in which the body is lacquered with a coating of a vulcanized silicon elastomer.

4. A prosthetic device as claimed in claim 1, in which the body is provided with anchoring formations.

5. A prosthetic device as claimed in claim 4, in which the anchoring formations include serrations on the edge of the body.

6. A prosthetic device as claimed in claim 4, in which the anchoring formations include wedge-shaped projections on the surface of the body intended to be in contact with the inner wall of the prostatic urethra.

7. A prosthetic device as set forth in claim 1 wherein said body has a plurality of perforations in a distal zone thereof for a flow of bodily secretions therethrough.

8. A prosthetic device as set forth in claim 7 having a plurality of anchoring formations on at least one of each side of said body and an outer surface of said body for anchoring in a urethra.

9. A prosthetic device for insertion in a urethra comprising a planar tongue-shaped body, said body being made of resilient material to permit resilient deformation of two sides thereof to impart a channel-shaped profile to said body for maintaining an open lumen in a urethra;
    a plurality of anchoring formations along each said side of said body for anchoring in a urethra; and
    a plurality of anchoring formations on an outer surface of said body for anchoring in a urethra.

10. A prosthetic device as set forth in claim 9 which further comprises a plurality of performations in said body to permit flow of prostatic secretions therethrough.

11. A prosthetic device as set forth in claim 9 wherein said anchoring formations on said sides are serrations.

12. A prosthetic device as set forth in claim 9 wherein said anchoring formations on said outer surface are wedge-shaped projections.

13. A prosthetic device as set forth in claim 9 wherein said body is made of a physiologically acceptable elastomeric polymer.

14. A prosthetic device as set forth in claim 9 which further comprises a coating of vulcanized silicon elastomer on said body.

* * * * *

UNITED STATES PATENT AND TRADEMARK OFFICE
CERTIFICATE OF CORRECTION

PATENT NO. : 5,069,660

DATED : December 3, 1991

INVENTOR(S) : David S. Grantham

It is certified that error appears in the above-identified patent and that said Letters Patent is hereby corrected as shown below:

Column 2, line 54, change "44" to --42--.

Signed and Sealed this

Fourteenth Day of September, 1993

Attest:

BRUCE LEHMAN

*Attesting Officer*  *Commissioner of Patents and Trademarks*